United States Patent [19]

Coval et al.

[11] Patent Number: 5,166,379

[45] Date of Patent: Nov. 24, 1992

[54] SYNTHESIS OF COMPOUNDS WITH BIOLOGICAL ACTIVITY, AND METHODS OF USE

[75] Inventors: Steve Coval, Ithaca, N.Y.; Gabriel Saucy, Vero Beach, Fla.; Richard D. Wood, Silver Springs, Md.; Ranjit C. Desai, East Greenbush, N.Y.; Geewananda P. Gunawardana; Ross E. Longley, both of Vero Beach, Fla.; Neal Burres, Highland Park, Ill.

[73] Assignee: Harbor Branch Oceanographic Institution, Inc., Fort Pierce, Fla.

[21] Appl. No.: 481,488

[22] Filed: Feb. 16, 1990

[51] Int. Cl.$^5$ .................... C07C 67/02; C07C 41/00; C07C 43/00

[52] U.S. Cl. ............................ 254/224; 554/223; 560/261; 568/687

[58] Field of Search .................. 568/687; 560/261; 554/223, 224; 514/549, 722, 738, 739

[56] References Cited

PUBLICATIONS

Castiello, D., G. Cimino, S. De Rosa, S. De Stefano, and G. Sodano (1980), "High Molecular Weight Polyacetylenes from the Nudibranch *Peltodoris atromaculata* and the Sponge *Petrosia ficiformis*," *Tetrahedron Letters* 21:5047–5050.

Cimino, G., A. DeGiulio, S. De Rosa, S. De Stefano, and G. Sodano (1985) "Further High Molecular Weight Polyacetylens from the Sponge *Petrosia ficiformis*," *J. Natural Products* 48(1):22–27.

Quinoa, E., and P. Crews (1988) "Melynes, Polyacetylene Constituents from a Vanuatu Marine sponge," *Tetrahedron Letters* 29(17):2037–2040.

Cimino, G., A. Crispino, S. De Rosa, S. De Stefano, and G. Sodano (1981), "Polyacetylenes from the spongs *Petrosia ficiformis* found in dark caves," *Experientia* 37:924–926.

Fusetani, N., Y. Kato, S. Matsunaga, and K. Hashimoto (1983), "Bioactive Marine Metabolites III, A Novel Polyacetylene Alcohol, Inhibitor of Cell Division in Fertilized Sea Urchin Eggs, from the Marine Sponge *Tetrosia* sp.," *Tetrahedron Letters* 24(27):2771–2774.

Wright, A. E., O. K. McConnell, S. Kohmoto, May S. Lui, Winnie Thompson, and K. M. Snader (1987), "Duryne, a New Cytotoxic Agent from the Marine Sponge *Cribrochalina dura*," *Tetrahedron Letters* 28(13):1377–1380.

Rao et al. Chem. Abstracts, vol. 111; No. 19; 173571a (1989).

Huche, M. Chem. Abstracts, vol. 86; No. 7; 42890w (1977).

Huche, M. et al. Chem. Abstracts, vol. 83; No. 9; 79336j (1975).

Huche et al. Chem. Abstracts, vol. 80; No. 15; 81970t (1974).

Rotem, M., and Y. Kashman (1979) "New Polyacetylenes from the Spronge *Siphonochalina* sp.," *Tetrahedron Letters* 34:3193–3106.

Fusetani, N., M. Sugano, S. Matsunaga, and K. Hashimoto (1987) "H,K-ATPase Inhibitors from the Marine Sponge *Siphonochalina truncata*: Absolute Configuration of Siphonodial and Two Related Metabolites," *Tetrahedron Letters* 28(37):4311–4312.

Hansen, L., and P. M. Boll (1986) "Polyacetylenes in Araliaceae: Their Chemisty, Biosynthesis, and Biological Significance," *Phytochemistry* 25(2):285–293.

*Canadian J. Microbiology*, vol. 31, 129–133 (1985).

Shi et al. Chem. Abstract; vol. 108; No. 21; 187023y (1988).

*Primary Examiner*—Johann Richter
*Attorney, Agent, or Firm*—Saliwanchik & Saliwanchik

[57] ABSTRACT

This invention relates to the methods for the synthesis and use of acetylenic carbinols and their analogs, having various immunomodulatory properties in vitro and in vivo.

5 Claims, No Drawings

SYNTHESIS OF COMPOUNDS WITH BIOLOGICAL ACTIVITY, AND METHODS OF USE

BACKGROUND OF THE INVENTION

Several classes of non-cyclic acetylenic compounds have been isolated from terrestrial plants as well as from marine organisms. Most of these compounds fall into the basic category referred to as the polyacetylenic compounds, having more than one acetylenic moiety. Several groups have reported the isolation of these polyacetylenic compounds from marine organisms. The acetylenic carbinols identified to date from marine organisms have been shown to contain more than one acetylenic carbinol moieties. See the following publications:

- Cimino, G., A. Crispino, S. De Rosa, S. De Stefano and G. Sodano (1981) "Polyacetylenes from the sponge *Petrosia ficiformis* found in dark caves," Experientia 37:924-926.
- Fusetani, N., Y. Kato, S. Matsunaga and K. Hashimoto (1983) "Bioactive marine metabolites III. A novel polyacetylene alcohol, inhibitor of cell division in fertilized sea urchin eggs, from the marine sponge *Tetrosia* sp.," Tetrahedron Letters, 24 (27):2771-2774.
- Wright, A. E., O. J. McConnell, S. Kohmoto, M. S. Lui, W. Thompson and K. M. Snader (1987) "Duryne, a new cytotoxic agent from the marine sponge *Cribrochalina dura*," Tetrahedron Letters, 28 (13):1377-1380.
- Castiello, D., G. Cimino, S. De Rosa, B. De Stefano and G. Sodano (1980) "High molecular weight polyacetylenes from the nudibranch *Peltodoris atromaculata* and the sponge *Petrosia ficiformis*," Tetrahedron Letters 21:5047-5050.
- Cimino, G., A. DeGiulio, S. De Rosa, S. De Stefano and G. Sodano (1985) "Further high molecular weight polyacetylenes from the sponge *Petrosia ficiformis*," J. Natural Products, Vol. 48, 1:22-27.
- Quinoa, E. and P. Crews (1988) "Melynes, polyacetylene constituents from a Vanuatu sponge," Tetrahedron Letters, 29 (17):2037-2040.
- Rotem, M. and Y. Kashman (1979) "New polyacetylenes from the sponge *Siphonochalina* sp.," Tetrahedron Letters 34:3193-3106.
- Fusetani, N., M. Sugano, S. Matsunaga and K. Hashimoto (1987) "H,KATPase inhibitors from the marine sponge *Siphonochalina truncata*: Absolute configuration of siphonodiol and two related metabolites," Tetrahedron Letters, 28 (37):4311-4312.
- Hansen, L. and P. M. Boll (1986) "Polyacetylenes in Araliaceae: Their chemistry, biosynthesis and biological significance," Phytochemistry, 25 (2):285-293.

The compounds of the subject invention are clearly different from the prior art as follows:

(1) The invention compounds are non-cyclic monoacetylenic carbinols;
(2) The invention compounds are unique in having a single terminal 3-ol, 4-en, 1-yne moiety attached to an alkyl chain; and,
(3) These invention compounds are the first report of such acetylenic compounds known to possess immunosuppressive activities.

BRIEF SUMMARY OF THE INVENTION

A series of acetylenic carbinols exemplified by structure I have been isolated from a marine sponge *Cribrocalina vasculum*. This invention relates to the methods for synthesis of these acetylenic carbinols and their analogs. These compounds have been found to exhibit immunomodulatory properties in vitro and in vivo.

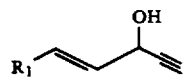

Structure I

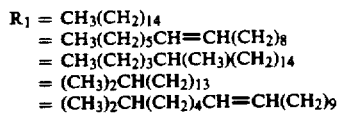

The subject invention concerns methods for synthesizing organic compounds with immunomodulatory properties. The synthesis of these compounds comprises the reaction of a suitable aldehyde with an ylide to give an $\alpha,\beta$-unsaturated aldehyde. The $\alpha,\beta$-unsaturated aldehyde is then reacted with appropriate acetylenic synthons to give the desired compounds.

DETAILED DESCRIPTION OF THE INVENTION

The present invention relates to methods for the synthesis of naturally occurring immunomodulatory acetylenic carbinols and their analogs. The method comprises the reaction of a suitable aldehyde with an ylide (e.g., $Ph_3P=CH-CHO$) to give an $\alpha,\beta$-unsaturated aldehyde which can then be reacted with suitable acetylenic synthons such as trimethylsilylacetylene (TMS—$C\equiv CH$) or lithium acetylide diamine complex (Li—$C\equiv CH$; EDA) under suitable conditions to give the desired compounds. The method is illustrated in Scheme 1.

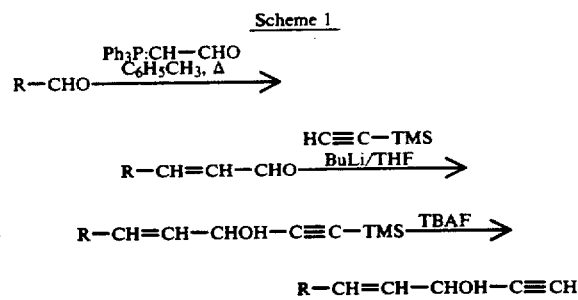

Synthesis of analogs of the parent acetylenic carbinols is also an aspect of the subject invention. In the syntheses of the analogs, the following structural features of the natural carbinol can be subjected to modification.

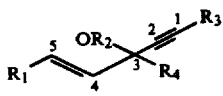

Structure II

As described in Structure I, the alkyl function ($R_1$) may be an unbranched or branched aliphatic chain either saturated or having one or more double bonds not conjugated with the C4-C5 double bond. This variation can be achieved by using the appropriate aldehyde as the starting material for the synthesis. The aldehydes can be obtained by the oxidation of commonly available alcohols using an oxidizing agent such as chromium trioxide or pyridinium chlorochromate in suitable solvents such as dichloromethane or other halogenated hydrocarbon solvents. The length of the chain may vary, provided the total number of carbons in the final acetylenic carbinol is between 12 and 30 atoms.

The hydroxy function on carbon 3 may be derivatized with suitable acids, acid chlorides, acid anhydrides, and carbamates, etc., to provide compositions having desired biological and physical properties. Methods for derivatizing $R_2$ are illustrated in Scheme 2.

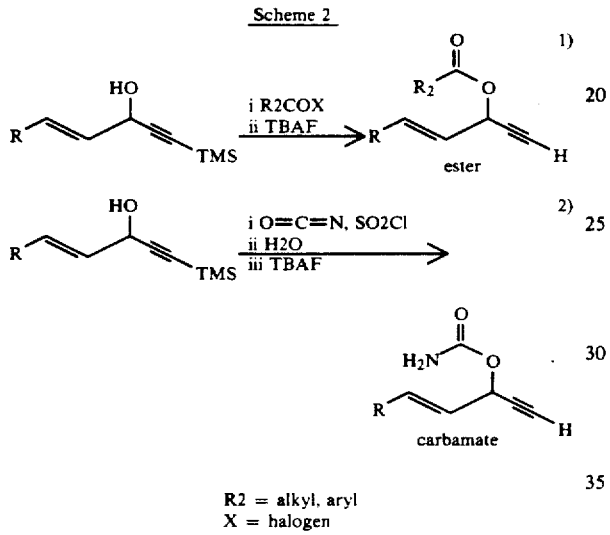

R2 = alkyl, aryl
X = halogen

The protons on the carbamate nitrogen could be substituted with alkyl or aryl functions to provide further derivatives.

The $R_3$ and $R_4$ groups shown in Structure II may also be derivatized via methods which are familiar to those skilled in the art. For example, $R_3$ may be modified to be CH, N, C—CH$_3$, or C(CH$_2$)$_n$CH$_3$, wherein n is an integer from 1 to 10.

The natural acetylenic carbinol was isolated in the (+) form and its optical purity was confirmed by Nuclear Magnetic Resonance (NMR) spectroscopy using chiral shift reagents (McCreary, Lewis, Wernick, and Whitesides [1974] J. Am. Chem. Soc. 96:1038) and measurement of its molecular rotation. While the synthetic route outlined in Scheme 1 yields a racemic mixture (±) of carbinols, both (+) and (−) forms of the acetylenic carbinol may be obtained in high optical purity by the following methods.

The racemic mixture of acetylenic carbinols obtained by the method shown in Scheme 1 may be resolved into optically pure (+) and (−) forms by converting them to diastereomeric esters of chiral acids or acid derivatives followed by fractional crystallization. The general methods for this process are reviewed by Klyaschitskii and Shvets (1972) Russ. Chem. Rev. 41:592, and the use of half acid phthlate amine salts for chiral resolution is described by Fried, Lin, Mehra, Kao and Dalven (1971) New York Acad. Sci. 180:38.

The racemic acetylenic alcohols, preferably their trimethylsilyl derivatives, could be oxidized using a suitable oxidizing agent such as pyridinium chlorochromate or chromium trioxide/pyridine, etc. The resulting ketones could then be reduced stereoselectively using chiral reducing agents to give optically pure or optically enriched compounds according to methods described by Midland, McDewell, Hatch, and Tramontano (1980) J. Am. Chem. Soc. 102:868.

The racemic mixtures of acetylenic carbinols may be resolved by high performance liquid chromatography either using chiral adsorbents alone or in combination with chiral solvents as eluents.

The enantiomerically pure acetylenic carbinols may be synthesized starting with suitable chiral synthons such as optically active sugars. The present method is illustrated by Scheme 3.

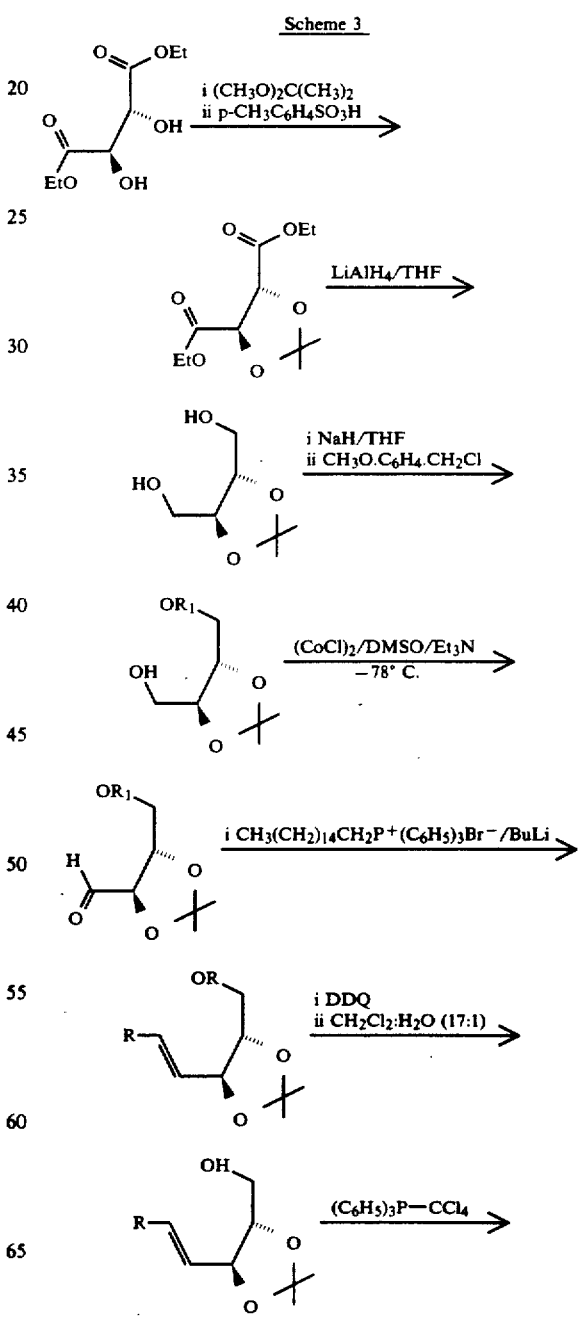

-continued
Scheme 3

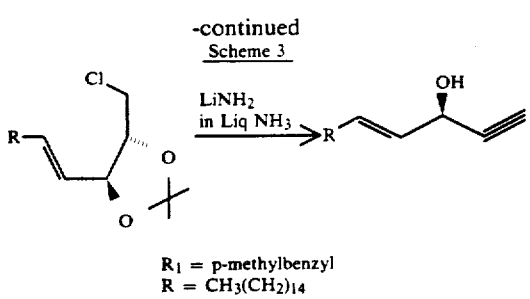

R₁ = p-methylbenzyl
R = $CH_3(CH_2)_{14}$

The natural acetylenic carbinols have a C4 trans double bond as shown by nuclear magnetic resonance experiments. However, it is possible to synthesize both trans and cis isomers of this compound. Further, it is possible to reduce the same double bond while retaining the immunomodulatory properties. The Wittig methodology, employed in the synthesis of these compounds (Scheme 2), gives a mixture of cis and trans α,β unsaturated aldehydes, the ratio depending on the experimental conditions (Schmidt and Zimmerman [1984] Tetrahedron Letters 25:1555 and the references therein). The resulting cis trans mixture of acetylenic carbinols may be separated by chromatographic methods using suitable adsorbents such as silver nitrate impregnated silica gel according to the methods described by Heath, Tumlinson, and Doolitle (1977) J. Chromatographic Sci. 15:10. In the present method the desired trans isomer was obtained exclusively by carrying out the Wittig reaction in a high boiling inert solvent like toluene.

Any combination of the above-mentioned structural features may be utilized to obtain compositions that would have the desired pharmacological utilities.

Following are examples which illustrate procedures, including the best mode, for practicing the invention. These examples should not be construed as limiting. All percentages are by weight and all solvent mixture proportions are by volume unless otherwise noted.

EXAMPLE 1

Synthesis of the Racemic Mixture of Straight Chain Unsaturated Acetylenic Carbinols of the Type $CH_3(CH_2)_nCHOHC\equiv CH$ The present method involves the reaction of a suitable aldehyde of the type $CH_3(CH_2)_nCHO$, where n=6 to 27, with a suitable acetylene such as trimethylsilylacetylene or lithium acetylide under suitable conditions. In the present method the preferred reagent is trimethylsilylacetylene. A solution of the reagent in an inert anhydrous solvent like diethyl ether or tetrahydrofuran was treated with butyl lithium at −70° C. under nitrogen and a solution of the aldehyde in the same solvent was added. The resulting trimethylsilyl derivative of the acetylenic carbinol was hydrolyzed using tetrabutylammoniumfluoride in tetrahydrofuran at 0° C. to give the acetylenic carbinol. The compound was purified by chromatography on silica gel eluting with hydrocarbon solvents systems.

Synthesis of racemic

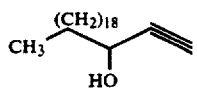

(a) Preparation of the aldehyde, $CH_3(CH_2)_{18}CHO$

A solution of 1-Eicosanol ($CH_3(CH_2)_{18}CHO$) (4.0 g) in dichloromethane (20 ml) was added to a rapidly stirred suspension of pyridinium chlorochromate ($C_5H_6N^+ClCrO_3$) (3.6 g) at room temperature. The reaction mixture was stirred for 3 hours, filtered through a short column of silica gel, and evaporated to dryness to give the crude aldehyde. The product was purified by crystallization using solvent systems containing dichloromethane and hexane, and the compound was characterized by NMR spectroscopy.

(b) Preparation of the TMS derivative, $CH_3(CH_2)_{18}CHOHC\equiv CTMS$

Anhydrous tetrahydrofuran was cooled to −70° C. under nitrogen, and trimethylsilylacetylene (1.2 g) was added, followed by a solution of butyl lithium (BuLi) in tetrahydrofuran (1.6M, 6.65 ml). The mixture was stirred for 0.5 hours, and a solution of the aldehyde (3.0 g) in THF (20 ml) was added slowly. The reaction mixture was stirred for 2 hours at −70° C. and quenched by addition of aqueous ammonium chloride. The reaction mixture was evaporated, redissolved in dichloromethane, and filtered through a short column of silica gel to give the product

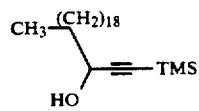

(c) Preparation of the acetylenic carbinol, $CH_3(CH_2)_{18}CHOHC\equiv CH$

The trimethylsilyl derivative (1.0 g) obtained from method 1 (b) was dissolved in THF (10 ml), cooled to 0° C. under nitrogen, and treated with a solution of tetrabutylammoniumfluoride in THF (1.0M, 6 ml). The reaction mixture was stirred for 1 hour, diluted with water, extracted with dichloromethane, dried ($Na_2SO_4$), and evaporated to give the acetylenic carbinol. The compound was purified either by column chromatography on silica gels or by HPLC on reverse phase C-18 support using methanol water as the solvent system.

The saturated straight chain acetylenic carbinols can be characterized by the following NMR spectral features.

FIG. 1.
NMR chemical shift values (in ppm)
for protons and carbons in CDCl3.

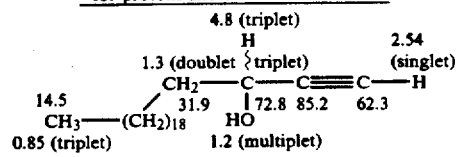

EXAMPLE 2

Synthesis of the Racemic, Unsaturated Acetylenic Carbinol

As illustrated in scheme 1, the present method involves the reaction of an aldehyde of the type $CH_3(CH_2)_nCHO$, n=6 to 27, prepared from a suitable alcohol by the method described in Example 1 (a) with a suitable ylide, according to Wittig methodology. In this example, the reagent of choice is (triphenyl phosphoranylidine)acetaldehyde. The resulting α,β unsaturated aldehyde is then converted to the acetylenic carbinol according to the methods described above.

EXAMPLE 3

Synthesis of CH$_3$(CH$_2$)$_{14}$CH:CH.CHO

In a flask fitted with a Dean-Stark condenser for removal of water, the aldehyde (CH$_3$(CH$_2$)$_{14}$CHO) (10.0 g), (triphenylphosphoranylidine)acetaldehyde (12.0 g) and toluene (100 ml) were heated under reflux for 24 hours under nitrogen. The solvents were removed, the solid was redissolved in hot diethyl ether and allowed to cool. The phosphate separated was filtered off, the solution was evaporated to dryness and chromatographed on silica gel using hexane and dichloromethane to remove small amounts of starting material and the doubly unsaturated aldehyde.

The α,β-unsaturated aldehyde thus obtained was converted to the acetylenic carbinol shown below through steps described in Example 1 (b) and (c).

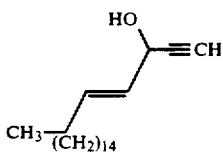

The physico-chemical properties and the biological profile of the synthetic compound were identical to those of the natural compound, except the molecular rotation, which is zero. The stereochemistry of the double bond in the α,β-unsaturated aldehyde and the acetylenic carbinol was deduced to be trans.

The unsaturated acetylenic carbinols can be characterized by the following NMR spectral features:

FIG. II
NMR chemical shift values (in ppm)
for protons and carbons in CDCl3.

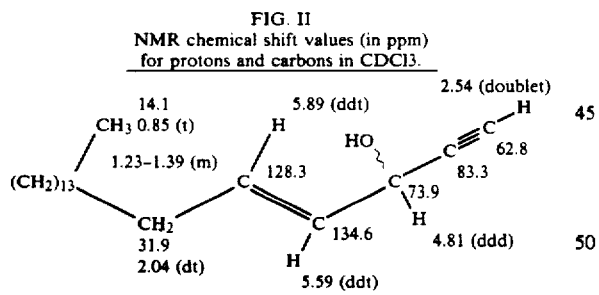

EXAMPLE 4

Chiral Synthesis of

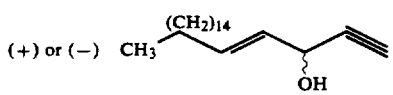

(a) Asymmetric reduction of acetylenic ketones to give enantomerically enriched (+) and (−) acetylenic carbinols.

The trimethylsilyl derivative of the racemic acetylenic carbinol (1.7 g) in dichloromethane (50 ml) was added into a rapidly stirred suspension of pyridinium chlorochromate (1.2 g) in dichloromethane at room temperature. The reaction mixture was stirred for 2 hours, filtered through a small column of silica, and evaporated to give the ketone CH$_3$(CH$_2$)$_{14}$COC≡C—TMS. The ketone was stereoselectively reduced according to the method described by Midland, Tramontano, Kazubski, Garham, Tsai, and Cardin (1984) Tetrahedron 40:1371, as follows. A solution of (+) alpine borane (purchased from Aldrich Chemical Company) was maintained at 0° C. in a nitrogen atmosphere and a solution of the ketone in THF was injected. The reaction mixture was stirred at 0° C. for 20 hours, and acetaldehyde was added. The solvents were removed under vacuum, and the pinene was removed by applying a 0.05 mm vacuum while heating the reaction mixture to 40° C. The residue was dissolved in diethyl ether, cooled in ice, and treated with ethanolamine. The precipitate was filtered off and the filtrate was washed with a saturated NaCl solution, dried over Na$_2$SO$_4$, and evaporated to dryness to enantomerically enriched acetylenic carbinol. The enantomeric excess (ee) was estimated by NMR spectroscopy according to the method described by McCreary, Lewis, Wernick, and Whitesides (1974) J. Am. Chem. Soc. 96:1038. Both (+) and (−) carbinols were obtained in 60–65% enantomeric excess using (+) or (−) alpine borane as the reducing agent respectively.

EXAMPLE 5

Acetylation of CH$_3$(CH$_2$)$_{14}$CH.CH.CHOH.C:CH

A solution of the TMS derivative of the acetylenic carbinol (1.0 g), obtained from method 2 (a), in pyridine (1 ml) was treated with acetic anhydride (2 ml), left at room temperature for 24 hours, and the reagents were removed under vacuum. The residue was dissolved in THF, hydrolyzed according to the method described in 1 (c), and purified by chromatography on silica gel to give

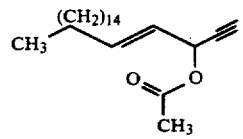

EXAMPLE 6

Biological Properties of Acetylenic Carbinols and Their Derivatives

The synthetic acetylenic carbinols were assayed to determine their immunomodulatory and antitumor properties. The assays conducted are described below.

DETAILED DESCRIPTION OF BIOLOGICAL ASSAYS

I. Mixed Lymphocyte Reaction

1. Murine splenocyte suspensions were prepared separately from BALB/c and C57BL/6J mice. Spleens were aseptically removed and homogenized in RPMI-1640 tissue culture medium (TCM), supplemented with 10% fetal calf serum, 2% 1-glutamine, 15 mM HEPES, 1% antibiotic-antimycotic solution, and 25 μg/ml gentamicin (GIBCO). The cell concentrations were adjusted to 2.5×10$^6$ cells/ml. Aliquots of each cell population were removed to separate tubes, and the remaining two cell suspensions combined to one tube.
2. Serial, $\log_{10}$ dilutions of the pure compound were made in absolute ethanol, and 10 μl of each dilution was added to wells of microtiter test plates, and allowed to dry.
3. A volume of 0.2 ml of the combined splenocyte suspensions was added to triplicate test wells. Positive control wells received combined splenocyte suspensions in the absence of the test compounds. Negative control wells consisted of separate (not mixed) splenocyte suspensions cultured in the absence of the test compounds.
4. Plates were incubated in 5% $CO_2$ at 37° C. for 86 hours.
5. A volume of 0.05 ml of $^3$H-thymidine (20 μCi/ml) was added to each well, and the plates were incubated in 5% $CO_2$ at 37° C. for an additional 5 hours.
6. The contents of each well of the microtiter plates were harvested onto glass fiber filter strips, and the resulting filter discs placed in scintillation vials to which 2.0 ml of scintillation fluid was added.
7. The amount of incorporated $^3$H-thymidine was determined by counting the vials in a liquid scintillation counter.
8. Triplicate counts were averaged, and the data reported as a percentage of the positive control. A value of less than 10% of the positive control MLR with a corresponding LCV value of >60% suggest optimal immunosuppressive effects of the compound. A value of greater than 150% of the positive MLR control with a corresponding LCV value of >75% indicates immunostimulatory effects of the compound.

II. Lymphocyte Viability Assay

1. Compounds were similarly tested in parallel with the MLR to determine their toxic effects on lymphoid cells using the lymphocyte viability assay (LCV).
2. Serial, $\log_{10}$ dilutions of the pure compound were made in absolute ethanol, and 10 μl of each dilution was added to wells of microtiter test plates, and allowed to dry.
3. Murine splenocyte suspensions were prepared from BALB/c mice. Spleens were aseptically removed and homogenized in RPMI-1640 tissue culture medium (TCM), supplemented with 10% fetal calf serum, 2% l-glutamine, 15 mM HEPES, 1% antibiotic-antimycotic solution, and 25 μg/ml gentamicin (GIBCO). The cell concentrations were adjusted to $2.5 \times 10^6$ cells/ml.
4. A volume of 0.2 ml of the splenocyte suspension was added to replicate test wells. Positive control wells received splenocyte suspensions in the absence of the test compounds.
5. Plates were incubated at 37° C. for 86 hours. At the end of the incubation period, a volume of 75 μl of a 2.0 mg/ml solution of MTT was added to each well, and the plates were returned to the incubator for an additional 5 hours.
6. The supernatants from each microwell were then removed, and a volume of 200 μl of isopropanol was added and the contents mixed.
7. Values were obtained by comparing the optical densities (determined at 570 and 650 nm) of wells containing the test compounds with those of wells containing cells and medium only (positive control). The results are expressed as a percentage of the positive control.
8. Replicate counts were averaged, and the data reported as a percentage of the positive control. An LCV value of less than 60% of the positive control is an indication of cytotoxicity of the test compounds for lymphoid cells.

III. Graft vs. Host (GVHR) In Vivo Activity

1. Donor mice (BALB/c) were sacrificed, spleens removed, and spleen cell suspensions prepared in tissue culture medium.
2. The above splenocyte suspension was adjusted to $10.0 \times 10^7$ cells/ml.
3. Mice were treated with varying dosages of the test compound. The test dosages used were previously determined to be non-toxic in acute toxicity assays. Treatment consisted of intraperitoneal injections, daily for 7 days. Dosages were calculated on a mg per kg body weight basis.
4. On day 1 of the first treatment regimen, recipient mice (CB6) were injected intraperitoneally with 0.50 ml ($50.0 \times 10^6$) of the donor (BALB/c) splenocyte suspension.
5. Controls consisted of the following:
   POS—mice receiving BALB/c splenocytes (Positive Control)
   SYN—mice receiving CB6 splenocytes (Syngeneic Control)
   CYP—mice receiving Cyclophosphamide (100 mg/kg) and BALB/c splenocytes
   CYA—mice receiving Cyclosporine A (250 mg/kg) and BALB/c splenocytes.
6. At the end of five days, recipient mice were sacrificed, weighed, and spleens removed and weighed.
7. A spleen index of 1.0 was assigned to the mean spleen weights (adjusted to body weight) of the SYN controls. The spleen index of treated mice was determined by comparing the spleen weights of those mice with that of the POS control. As a general rule, a spleen index of the positive control (no compound) which was greater than or equal to 1.3 was considered a positive response. As a general rule, a spleen index of less than the positive control is indicative of an immunosuppressive (ID) compound.

IV. Antitumor Methodology

To assess the antiproliferative effects against P388 cells, 200 μl cultures (96-well tissue culture plates, Nunc, Denmark) were established at $1 \times 10^5$ cells/ml in drug-free medium or medium containing the pure compounds/crude extracts at a final dilution or 1:500 and at various concentrations. Solvent for all dilutions was methanol, which was removed from plates under vacuum. All experimental cultures were initiated in media containing Gentamicin sulfate (50 μg/ml; Schering Corporation, Kenilworth, NJ). After 48 hour exposures, P388 cells were enumerated using 3-[4,5-dimetylthiazol-2-yl]-2,5-diphenyltetrazolium bromide (MTT) as described below (Alley, M.C. et al. [1988] Cancer Res. 48:589).

To quantitate the effects of pure compounds/crude extracts on cell proliferation, 75 μl of warm growth medium containing 5 mg/ml MTT was added to each well, cultures were returned to the incubator, and were left undisturbed for 90 minutes. To spectrophotometrically quantitate formation of reduced formazan, plates were centrifuged (900×g, 5 minutes), culture fluids removed by aspiration, and 200 μl of acidified isopropanol (2 ml concentrated HCl/liter isopropanol) added per well. The absorbance of the resulting solutions were measured at 570 nm with a plate reader (MR700 Microplate Reader, Dynatech Laboratories, Chantilly, VA). The absorbance of test wells was divided by the absorbance of drug-free wells, and the concentration of agent that resulted in 50% of the absorbance of untreated cultures was determined by linear regression of logit-transformed data (Finney, D. J. *Statistical Method in Biological Assay*, 3rd ed., Charles Griffin Co., London, 1978, pp. 316–348). A linear relationship between P388 cell number and formazan production was found over the range of cell densities observed in these experiments.

The results of these assays are summarized in Table 1 and 2. It is clear from these tables that each of the compounds tested produced % MLR of less than 10% at some concentration. However, as a general rule, for a compound to be considered optimal as an immunosuppressive agent, the % MLR of less than 10 should be accompanied by a % LCV which is greater than 60. Tables 1 and 2 identify the best immunosuppressive compounds as well as the concentration(s) at which this activity was observed. Tables 1 and 2 also report the P388 $IC_{50}$ of most of the compounds. This value is an indication of the antitumor activity of the tested compound.

EXAMPLE 7

The results of the in vivo GVHR studies provide further insight into the immunomodulatory properties of the synthetic acetylenic carbinols. These results are shown in Tables 3 through 5.

The results presented in Table 3 demonstrate that mice treated with 150.0 mg/kg of the C-20 acetylenic alcohol were suppressed (81%) in their ability to mount a graft vs host reaction as measured by a reduction in the size of their spleens (spleen index) compared to that of untreated mice receiving allogenic grafts. This dosage level, however, was associated with some degree of cytotoxicity (2/5 survivors). Subsequent dosages resulted in an inverse dose response curve, with 25.0 mg/kg animals displaying suppressed responsiveness (45%) compared to control. Cyclophosphamide and Cyclosporine A-treated mice, which were used as suppressive drug controls, also displayed the characteristic suppression of the splenomegaly response. The results of this study indicated that the racemic C-20 acetylenic alcohol could mediate the suppression of the GVHR, as measured by a decrease in the normal splenomegaly response observed in mice grafted with allogenic spleen cells.

The results summarized in Table 4 demonstrate that mice treated with 50.0 mg/kg of the C-19 acetylenic alcohol were suppressed (49%) in their ability to mount a graft vs host reaction as measured in the spleen index compared to that of untreated mice receiving allogenic grafts.

The results summarized in Table 5 indicate that the C-12 acetylenic alcohol was effective in suppressing the GVHR, as measured by the suppression of the positive control spleen index. The compound demonstrated suppressive activity in the GVHR at all dosages tested, with no associated toxicity as measured by survival of treated recipients.

EXAMPLE 8

FORMULATION AND ADMINISTRATION

The compounds of the invention are useful for various non-therapeutic and therapeutic purposes. It is apparent from the testing that the compounds of the invention are effective for immunomodulation and for controlling tumor growth. Also, the compounds can be used as ultraviolet screeners in the plastics industry since they effectively absorb UV rays. As disclosed herein, they are also useful therapeutically for treating tumors in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

| | Summary of In Vitro IM-Data on Synthetic Alcohols | | | | | | |
|---|---|---|---|---|---|---|---|
| | CONCENTRATION (μg/ml) | | | | | | |
| | 0.05 | 0.2 | 0.8 | 3.1 | 12.5 | 50 | |
| Compound | (% MLR/% LCV) | | | | | | P388 $IC_{50}$ (μg/ml) |
| $CH_3(CH_2)_{14}CHO$ | 59/237 | 94/182 | 80/161 | 73/202 | 36/153 | 0/132 | 44.0 |
| $CH_3(CH_2)_{14}CH=CH-CHO$ | 150/130 | 105/175 | 135/181 | 146/186 | 0/89 | 0/5 | 15.1 |
| $CH_3(CH_2)_{14}CH=CH-CHOH-C\equiv CH$ | 0/63 | 0/42 | 0/20 | 0/19 | 0/19 | 0/11 | 9.4 |
| $CH_3(CH_2)_{14}CH=CH-CHOAc-C\equiv CH$ | 73/58 | 0/53 | 0/30 | 0/30 | 0/23 | 0/11 | 100 |
| $CH_3(CH_2)_{14}CH=CH-CHOH-C\equiv C-CH_3$ | 137/154 | 143/107 | 83/75 | 0/86 | 0/67 | 0/60 | 200 |
| $CH_3(CH_2)_{14}CH=CH-COH(CH_3)-C\equiv CH$ | 152/53 | 161/107 | 171/118 | 115/109 | 65/54 | 0/5 | 67.0 |
| $CH_3(CH_2)_4CH=CH-CHOH-C\equiv CH$ | 112/109 | 14/121 | 82/119 | 0/89 | 0/65 | 0/7 | 74.0 |
| $CH_3(CH_2)_8CH=CH-CHOH-C\equiv CH$ | 120/35 | 0/44 | 0/30 | 0/26 | 0/5 | 0/0 | 27.0 |

TABLE 1-continued

Summary of In Vitro IM-Data on Synthetic Alcohols

| Compound | CONCENTRATION (μg/ml) | | | | | | P388 IC$_{50}$ (μg/ml) |
|---|---|---|---|---|---|---|---|
| | 0.05 | 0.2 | 0.8 | 3.1 | 12.5 | 50 | |
| | | | (% MLR/% LCV) | | | | |
| $CH_3(CH_2)_{18}CH=CH-CHOH-C\equiv CH$ | 103/58 | 103/70 | 0/61 | 0/28 | 0/30 | 0/39 | 219 |
| $CH_3(CH_2)_{16}CHOH-C\equiv CH$ | 0/61 | 0/68 | 0/39 | 0/56 | 0/7 | 0/2 | 48.0 |
| $CH_3(CH_2)_{14}CH=CH-CHOH-C\equiv N$ | 60/132 | 89/135 | 85/161 | 80/144 | 0/77 | 0/37 | 28.0 |
| $CH_3(CH_2)_4CH=CH-CHOH-C\equiv C-(CH_2)_7CH_3$ | 127/128 | 135/119 | 122/105 | 64/86 | 0/28 | 0/14 | NT |
| $CH_3(CH_2)_{14}CH_2OH$ | 136/70 | 128/86 | 127/37 | 137/98 | 0/0 | 0/0 | 9.3 |

Bold lettering identifies % MLR <10% and % LCV >60%.

TABLE 2

Summary of In Vitro IM-Data on Synthetic Alcohols

| Compound | CONCENTRATION (μg/ml) | | | | |
|---|---|---|---|---|---|
| | 0.005 | 0.05 | 0.5 | 5.0 | 50.0 |
| | | | (% MLR/% LCV) | | |
| $CH_3(CH_2)_{15}CH=CHCOHC\equiv CH$ | | 13/78 | 0/78 | 0/17 | 0/13 |
| $CH_3(CH_2)_{15}CHOHC\equiv CH$ | 0/65 | 0/49 | 0/22 | 0/24 | 0/22 |
| $CH_3(CH_2)_{15}COC\equiv CH$ | | 114/91 | 7/89 | 0/47 | 0/34 |
| $CH_3(CH_2)_3CHOHC\equiv CH$ | | 89/117 | 136/116 | 47/0 | 0/61 |
| $CH_3(CH_2)_3CH=CH-CH=CH-CHOHC\equiv CH$ | | 134/103 | 0/72 | 0/14 | 0/29 |
| $CH_3(CH_2)_6CHOHC\equiv CH$ | | 117/72 | 130/85 | 131/70 | 108/61 |
| $CH_3(CH_2)_4CH=CHCH_2CH_2CHOHC\equiv CH$ | | 137/65 | 122/57 | 110/45 | 50/51 |
| $CH_3(CH_2)_{14}CHOHC\equiv CH$ | | 100/105 | 0/47 | 0/36 | 0/10 |
| $CH_3(CH_2)_{15}CHOHCH=CH_2$ | | 99/80 | 74/80 | 0/2 | 0/5 |

Bold lettering identifies % MLR <10% and % LCV >60%.

TABLE 3

Summary of In vivo GVHR Studies with a C-20 Acetylenic Alcohol

| $^a$Treatment | $^b$# Mice | $^c$Stim. Index | $^d$% Suppression |
|---|---|---|---|
| $^e$Acetylenic Alcohol (150.0 mg/kg) | 2 | 1.22 ± .03 | 81 |
| Acetylenic Alcohol (100.0 mg/kg) | 5 | 2.35 ± .15 | 0 |
| Acetylenic Alcohol (50.0 mg/kg) | 5 | 1.86 ± .18 | 25 |
| Acetylenic Alcohol (25.0 mg/kg) | 5 | 1.63 ± .25 | 45 |
| Cyclophosphamide (100 mg/kg) | 5 | .031 ± .001 | 160 |
| Cyclosporine A (200 mg/kg) | 5 | 0.86 ± .007 | 112 |
| Positive (Vehicle) | 5 | 2.15 ± .11 | 0 |

$^a$CB6F$_1$ mice (5 mice per group) were grafted with 5 × 10$^7$ BALB/c spelnocytes, i.p. on Day 0. Groups were injected, ii.p., with drug (or vehicle) on Days 1-6. Positive designates grafted mice receiving vehicle alone.
$^b$Number of surviving mice at end of experiment.

$$^c\text{Stimulation index (S.I.)} = \frac{\text{Spleen wt. of test group/Body wt. of test group}}{\text{Spleen wt. of syngeneic group/Body weight of syngeneic group}}$$

$$^d\% \text{ Suppression} = \frac{\text{(S.I. of Positive Control)} - \text{(S.I. of Test Group)}}{\text{(S.I. of Positive Control)} - \text{(S.I. of Syngeneic Group)}} \times 100$$

(Stimulation Index of Syngeneic group (CB6F$_1$->CB6F$_1$) = 100
$^e$CH$_3$(CH$_2$)$_{14}$CH=CH—CHOH—C≡CH

TABLE 4

Summary of In vivo GVHR Studies with a C-19 Acetylenic Alcohol

| $^a$Treatment | $^b$# Mice | $^c$Stim. Index | $^d$% Suppression |
|---|---|---|---|
| $^e$C-19 (200.0 mg/kg) | 2 | 3.61 | 0 |
| C-19 (150.0 mg/kg) | 5 | 2.27 | 4 |
| C-19 (100.0 mg/kg) | 5 | 2.56 | 0 |
| C-19 (50.0 mg/kg) | 5 | 1.67 | 49 |
| Cyclophosphamide (100.0 mg/kg) | 5 | 0.31 | 142 |
| Positive (Vehicle) | 5 | 2.15 | 0 |

$^a$CB6F$_1$ mice (5 mice per group) were grafted with 5 × 10$^7$ BALB/c spelnocytes, i.p. on Day 0. Groups were injected, ii.p., with drug (or vehicle) on Days 1-6. Positive designates grafted mice receiving vehicle alone.
$^b$Number of surviving mice at end of experiment.

$$^c\text{Stimulation index (S.I.)} = \frac{\text{Spleen wt. of test group/Body wt. of test group}}{\text{Spleen wt. of syngeneic group/Body weight of syngeneic group}}$$

$$^d\% \text{ Suppression} = \frac{\text{(S.I. of Positive Control)} - \text{(S.I. of Test Group)}}{\text{(S.I. of Positive Control)} - \text{(S.I. of Syngeneic Group)}} \times 100$$

(Stimulation Index of Syngeneic group (CB6F$_1$->CB6F$_1$) = 100
$^e$C-19 = CH$_3$(CH$_2$)$_{15}$CHOHC≡CH

TABLE 5

Summary of In vivo GVHR Studies with a C-19 Acetylenic Alcohol

| $^a$Treatment | $^b$# Mice | $^c$Stim. Index | $^d$% Suppression |
|---|---|---|---|
| $^e$C-12 (200.0 mg/kg) | 2 | 1.72 | 57 |
| C-12 (150.0 mg/kg) | 5 | 2.21 | 28 |
| C-12 (100.0 mg/kg) | 5 | 1.69 | 59 |
| C-12 (50.0 mg/kg) | 5 | 2.09 | 35 |
| Cyclophosphamide (100.0 mg/kg) | 5 | 0.31 | 132 |
| Positive (Vehicle) | 5 | 2.15 | 0 |

$^a$CB6F$_1$ mice (5 mice per group) were grafted with 5 × 10$^7$ BALB/c spelnocytes, i.p. on Day 0. Groups were injected, ii.p., with drug (or vehicle) on Days 1-6. Positive designates grafted mice receiving vehicle alone.
$^b$Number of surviving mice at end of experiment.

$$^c\text{Stimulation index (S.I.)} = \frac{\text{Spleen wt. of test group/Body wt. of test group}}{\text{Spleen wt. of syngeneic group/Body weight of syngeneic group}}$$

$$^d\% \text{ Suppression} = \frac{\text{(S.I. of Positive Control)} - \text{(S.I. of Test Group)}}{\text{(S.I. of Positive Control)} - \text{(S.I. of Syngeneic Group)}} \times 100$$

(Stimulation Index of Syngeneic group (CB6F$_1$->CB6F$_1$) = 100
$^e$C-12 = CH$_3$(CH$_2$)$_4$CH=CHCH$_2$CH$_2$OHC≡CH

We claim:

1. A compound having the following structural formula:

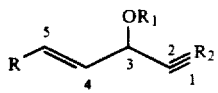

wherein R is an unbranched or branched aliphatic chain with 7 to 25 carbons, R is saturated or has one or two double bonds not conjugated with the C4–C5 double bond; $R_1$ is an alkyl or acyl function with 1 to 6 carbons; and $R_2$ is CH or C-CH$_3$.

2. The compound, according to claim 1, wherein R is selected from the group consisting of $CH_3(CH_2)_{14}$, $CH_3(CH_2)_5CH=CH(CH_2)_8$, $CH_3(CH_2)_3CH(CH_3)(CH_2)_{14}$, $(CH_3)_2(CH_2)_{13}$, and $CH_3)_2CH(CH_2)_{14}CH=CH(CH_2)_9$.

3. The compound selected from the group consisting of
(a) $CH_3(CH_2)_{14}CH=CH—CHO$;
(b) $CH_3(CH_2)_{14}CH=CH—CHOH—C\equiv CH$;
(c) $CH_3(CH_2)_{14}CH=CH—CHOAc—C\equiv CH$;
(d) $CH_3(CH_2)_{14}CH=CH—CHOH—C\equiv C—CH_3$;
(e) $CH_3(CH_2)_{14}CH=CH—COH(CH_3)—C\equiv CH$;
(f) $CH_3(CH_2)_4CH=CH—CHOH—C\equiv CH$;
(g) $CH_3(CH_2)_8CH=CH—CHOH—C\equiv CH$;
(h) $CH_3(CH_2)_{18}CH=CH—CHOH—C\equiv CH$;
(i) $CH_3(CH_2)_{16}CHOH—C\equiv CH$;
(j) $CH_3(CH_2)_4CH=CH—CHOH—C\equiv C—(CH_2)_7CH_3$;
(k) $CH_3(CH_2)_{14}CH_2OH$;
(l) $CH_3(CH_2)_{15}CH=CHCOHC\equiv CH$;
(m) $CH_3(CH_2)_{15}CHOHC\equiv CH$;
(n) $CH_3(CH_2)_{15}OC\equiv CH$;
(o) $CH_3(CH_2)_3CHOHC\equiv CH$;
(p) $CH_3(CH_2)_3CH=CH—CH=CH—CHOH—C\equiv CH$;
(q) $CH_3(CH_2)_6CHOHC\equiv CH$;
(r) $CH_3(CH_2)_4CH=CHCH_2CH_2CHOHC\equiv CH$;
(s) $CH_3(CH_2)_{14}CHOHC\equiv CH$; and
(t) $CH_3(CH_2)_{15}CHOHCH=CH_2$.

4. A process for treating a human or animal in need of immunosuppression which comprises administering to said human or animal an effective amount of a compound of claim 3.

5. The process, according to claim 4, wherein said compound is selected from the group consisting of
(a) $CH_3(CH_2)_{14}CH=CH—CHO$;
(b) $CH_3(CH_2)_{14}CH=CH—CHOH—C\equiv CH$;
(c) $CH_3(CH_2)_{14}CH=CH—CHOH—C\equiv C—CH_3$;
(d) $CH_3(CH_2)_4CH=CH—CHOH—C\equiv CH$;
(e) $CH_3(CH_2)_{16}CHOH—C\equiv CH$;
(f) $CH_3(CH_2)_{14}CH=CH—CHOH—C\equiv N$;
(g) $CH_3(CH_2)_{15}CH=CHCOHC\equiv CH$;
(h) $CH_3(CH_2)_{15}CHOHC\equiv CH$;
(i) $CH_3(CH_2)_{15}OC\equiv CH$;
(j) $CH_3(CH_2)_3CH=CH—CH=CH—CHOH—C\equiv CH$; and
(k) $CH_3(CH_2)_{14}CHOHC\equiv CH$.

* * * * *

UNITED STATES PATENT AND TRADEMARK OFFICE
CERTIFICATE OF CORRECTION

PATENT NO. : 5,166,379
DATED : November 24, 1992
INVENTOR(S) : Steve Coval et al It is certified that error appears in the above-identified patent and that said Letters Patent is hereby corrected as shown below:

Column 11, line 17, "Table" should read --Tables--.

Signed and Sealed this

Second Day of November, 1993

BRUCE LEHMAN

Attest:

Attesting Officer

Commissioner of Patents and Trademarks